(12) United States Patent
Chen (10) Patent No.: US 7,030,735 B2
(45) Date of Patent: Apr. 18, 2006

(54) WIRELESS MOTION MONITORING DEVICE INCORPORATING EQUIPMENT CONTROL MODULE OF AN EXERCISE EQUIPMENT

(76) Inventor: Yu-Yu Chen, 2Fl., No. 349, Wushing St., Shinyi Chiu, Taipei (TW) 110

( * ) Notice: Subject to any disclaimer, the term of this patent is extended or adjusted under 35 U.S.C. 154(b) by 74 days.

(21) Appl. No.: 10/755,268

(22) Filed: Jan. 13, 2004

(65) Prior Publication Data

US 2005/0159272 A1    Jul. 21, 2005

(51) Int. Cl.
*G08B 23/00* (2006.01)

(52) U.S. Cl. ............................. 340/323 R; 340/573.1; 482/8

(58) Field of Classification Search .......... 340/309.16, 340/323 R, 539.11, 573.1, 573.3, 573.6; 482/1, 8, 900, 901; 600/520, 523
See application file for complete search history.

(56) References Cited

U.S. PATENT DOCUMENTS 5,527,239 A * 6/1996 Abbondanza ................. 482/8
6,033,344 A * 3/2000 Trulaske et al. ............... 482/7
6,077,193 A * 6/2000 Buhler et al. .................. 482/8
6,132,337 A * 10/2000 Krupka et al. ................. 482/8
6,332,094 B1 * 12/2001 Gorman ....................... 600/520
6,790,178 B1 * 9/2004 Mault et al. ................. 600/300

* cited by examiner

*Primary Examiner*—Van T. Trieu
(74) *Attorney, Agent, or Firm*—Rosenberg, Klein & Lee (57) ABSTRACT

A wireless motion monitoring device adaptive to incorporate an equipment control module of an exercise equipment is provided to detect the motion signal of a user. The wireless motion monitoring device includes a motion signal receiving module electrically coupling to a circuit board of the equipment control module. A wireless motion signal detecting module is able to detect the motion signal of the user. The motion signal is transmitted by a wireless transmitter which is arranged in the wireless motion signal detecting module. A wireless receiver is arranged in the motion signal receiving module for receiving the motion signal transmitted by the motion signal detecting module. After the motion signal receiving module receives the motion signal transmitted from the motion signal detecting module, the motion signal is transmitted to the equipment control module of the exercise equipment and displayed on a display unit of the equipment control module.

17 Claims, 8 Drawing Sheets

WIRELESS MOTION MONITORING DEVICE INCORPORATING EQUIPMENT CONTROL MODULE OF AN EXERCISE EQUIPMENT

BACKGROUND OF THE INVENTION

1. Field of the Invention

The present invention relates to a motion signal detecting device, and more particularly to a wireless motion monitoring device that can be incorporated with an equipment control module of an exercise equipment for monitoring the motion of a user.

2. Description of the Prior Art

There are variety of body building devices and exercisers developed for people who live busily in the modern commercial society and require appropriate exercises. For a person to accurately control a moderate amount of exercise and monitor personal physical condition, various types of body/motion signal sensing devices have been researched and developed.

As indoor exercise equipment are usually arranged in a big enough space and well supplied with power source, they generally possess multiple functions and are more powerful than outdoor exercise equipment. On the other hand, the indoor exercise equipment generally have wires and are bulky, that make they inconvenient to use in some situations. Hence, some simple body/motion signal detecting devices, that are portable and easy to use, are developed. Take for an example. Pedometer is a simple and portable motion signal detecting device that is popular for use. To use the pedometer, the user just simply fits it to his body. Thereby, the user can measure a distance that he walks, jogs or runs, or an accumulated number of jumping.

However, pedometer can only display the accumulated number of paces that the user advances on the display unit of the pedometer. The data cannot be incorporated or transmitted to other exercise equipment. It is frequent found that in a fitting center where a variety of exercise equipment are available, many exercisers perform more than one exercise e.g. jogging and biking. Anyway, he is not able to monitor all his exercising data simultaneously at the same equipment.

SUMMARY OF THE INVENTION

Thus, a primary object of the present invention is to provide a wireless motion monitoring device that is able to incorporate with an equipment control module of an exercise equipment. The wireless motion monitoring device measures the paces that the user advances and transmits the data to the equipment control module of the exercise equipment for displaying.

Another object of the present invention is to provide a wireless motion monitoring device that is capable to transmit the detected pace data via a wireless transmitter to the equipment control module of the exercise equipment.

A further object of the present invention is to provide an exercise equipment capable of receiving the pace signal wirelessly. The equipment control module of the exercise equipment is coupled with a wireless motion signal receiving module that can receive the pace signal wirelessly. The pace signal is displayed in a display unit at the exercise equipment.

To achieve the above and other objects, in accordance with the present invention, there is provided with a wireless motion monitoring device for incorporating with an equipment control module of an exercise equipment for monitoring the paces of a user. The wireless motion monitoring device includes a motion signal receiving module which has an interface slot for electrically coupling to a circuit board of the equipment control module. A wireless receiver is arranged in the motion signal receiving module. A wireless receiver is arranged in the motion signal receiving module. A wireless pedometer module is able to detect at least one pace signal of the user. The pace signal is transmitted by radio frequency or infrared ray by a wireless transmitter which is arranged in the wireless pedometer module. After the wireless receiver receives the pace signal from the wireless pedometer module, the pace signal is transmitted via the interface slot to a control circuit of the equipment control module which displays the pace signal on a display unit of the equipment control module.

BRIEF DESCRIPTION OF THE DRAWINGS

The present invention will be apparent to those skilled in the art by reading the following description of the best mode and a preferred embodiment of a device for carrying out the present invention, with reference to the attached drawings, in which.

DETAILED DESCRIPTION OF THE PREFERRED EMBODIMENTS

Figure 1:
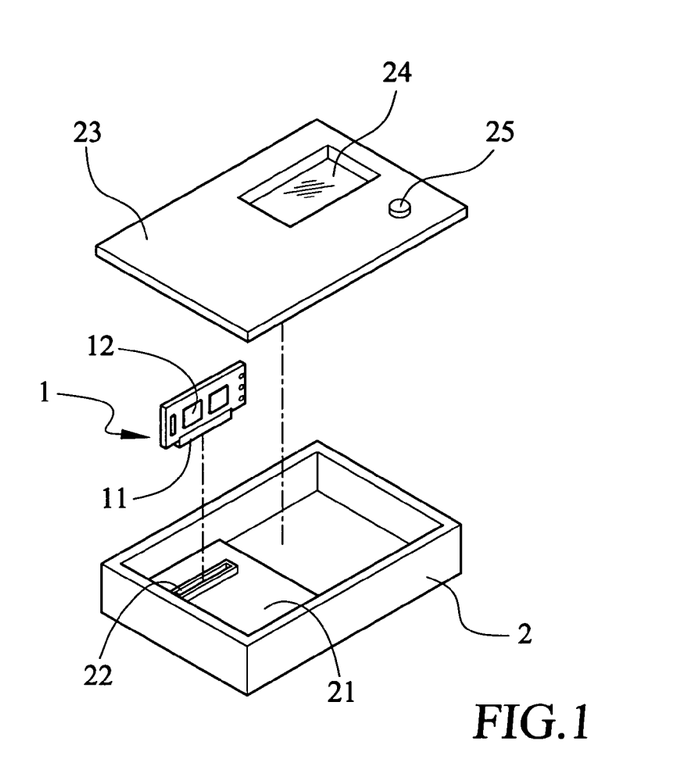
FIG. 1 is perspective view showing a motion signal receiving module incorporating with an equipment control module of an exercise equipment constructed in accordance with a first embodiment of the present invention.

Please refer to the drawings and in particular to FIG. 1 which is perspective view showing a motion signal receiving module of a wireless motion monitoring device constructed in accordance with a first embodiment of the present invention incorporates an equipment control module. As shown, the motion signal receiving module 1 is in the form of interface card which may be electrically connected to a circuit board 21 arranged in the equipment control module 2. The equipment control module 2 includes a control circuit arranged on the circuit board 21 for receiving signals generated by an exercise equipment or controlling the operation of the exercise equipment. The connection between the motion signal receiving module 1 and the circuit board 21 can be accomplished by plugging or by means of a connection edge or cable.

In this embodiment, a connector socket 22 is mounted on and electrically connected to the circuit board 21 of the equipment control module 2. Correspondingly, a connection edge 11 is formed on a lower edge of the motion signal receiving module 1. So, the motion signal receiving module 1 can be plugged in the connector socket 22 of the circuit board 21 by means of its connection edge 11.

The motion signal receiving module 1 is provided with electric components 12 such as antenna and receiving circuit thereon. The equipment control module 2 is provided with a display unit 24 on a panel 23 thereof for displaying data. In addition, a transmission activating button 25 is arranged on the panel 23 of the equipment control module 2 for activating the transmission of a pace signal from a motion signal detecting device.

Figure 2:
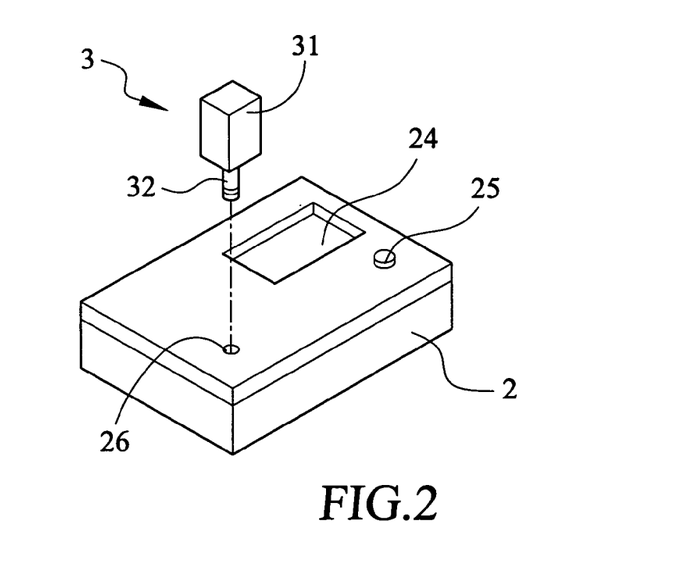
FIG. 2 is a perspective view of a second embodiment of the motion signal receiving module of the present invention.

FIG. 2 is a perspective view of a motion signal receiving module in accordance with a second embodiment of the present invention. In this embodiment, the motion signal receiving module 3 is in the form of plug having a plug casing 31. The plug casing 31 is formed with an internal space for accommodation of a number of electric components such as circuit board, antenna, and receiving circuit. A plugging end 32 is extended from an end of the plug casing 31 adapted to be plugged into a socket 26 formed on the equipment control module 2.

Figure 3:
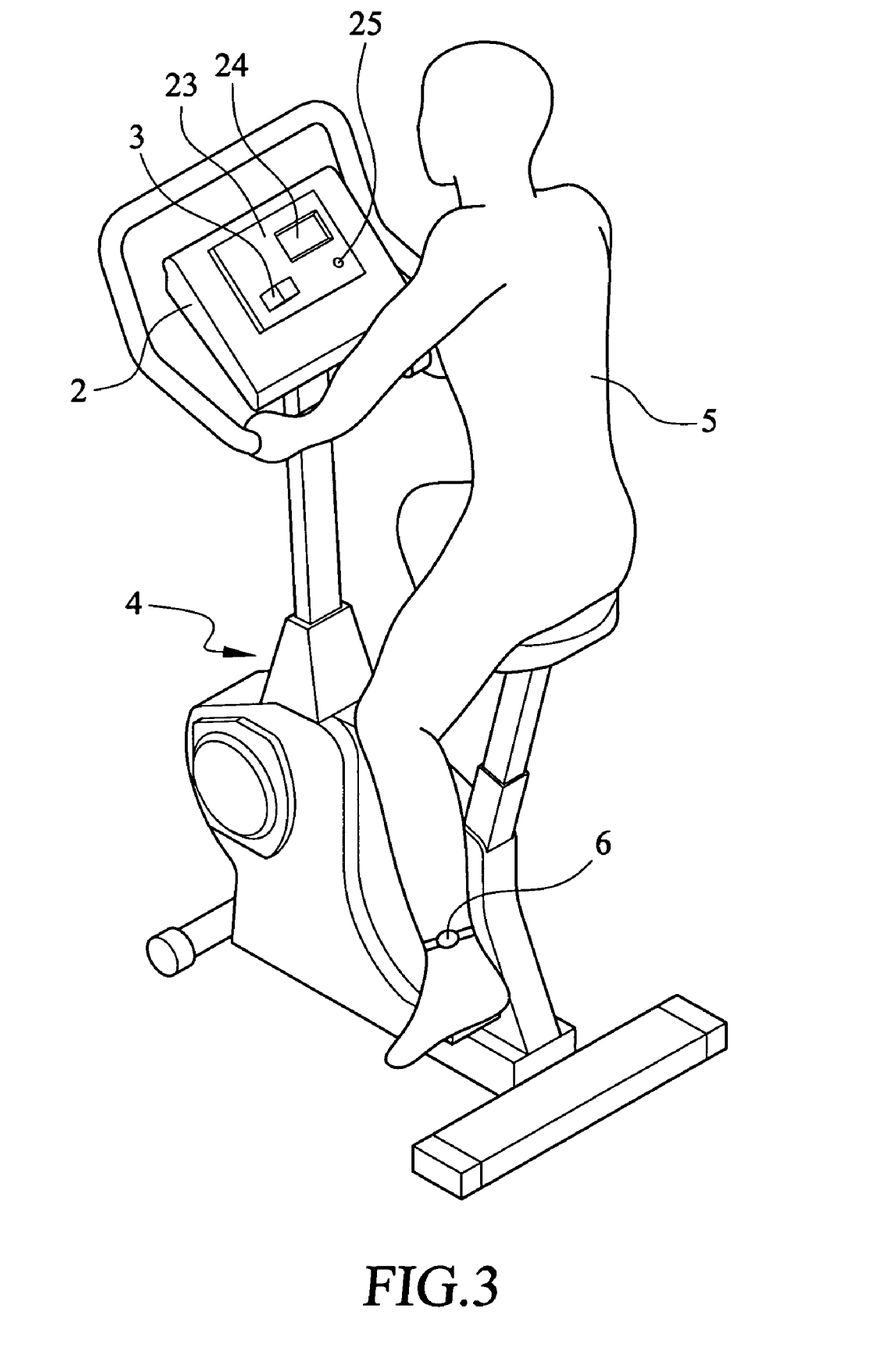
FIG. 3 is a perspective view showing that the wireless motion monitoring device of the present invention is applied to an indoor exercise bicycle.

FIG. 3 is a perspective view showing that the wireless motion monitoring device of the present invention is applied to an indoor exercise bicycle. Of course, the wireless motion monitoring device can also be incorporated with a stepper or a climbing machine. In the application, the equipment control module 2 of the exercise bicycle 4 incorporates the plug form motion signal receiving module 3 as shown in FIG. 2. Alternatively, the equipment control module 2 of the exercise bicycle 4 may incorporate the card form motion signal receiving module 1 as shown in FIG. 1.

To monitor the user's motion signal, the wireless motion monitoring device includes a motion signal detecting device that can detect a motion of the user. Accordingly, to provide a motion signal including pace signal of the user to be displayed on an exercise equipment, the wireless motion monitoring device includes a wireless pedometer module which measures the number of paces that the user walks, jogs or runs on the ground or on the exercise equipment.

Figure 4:
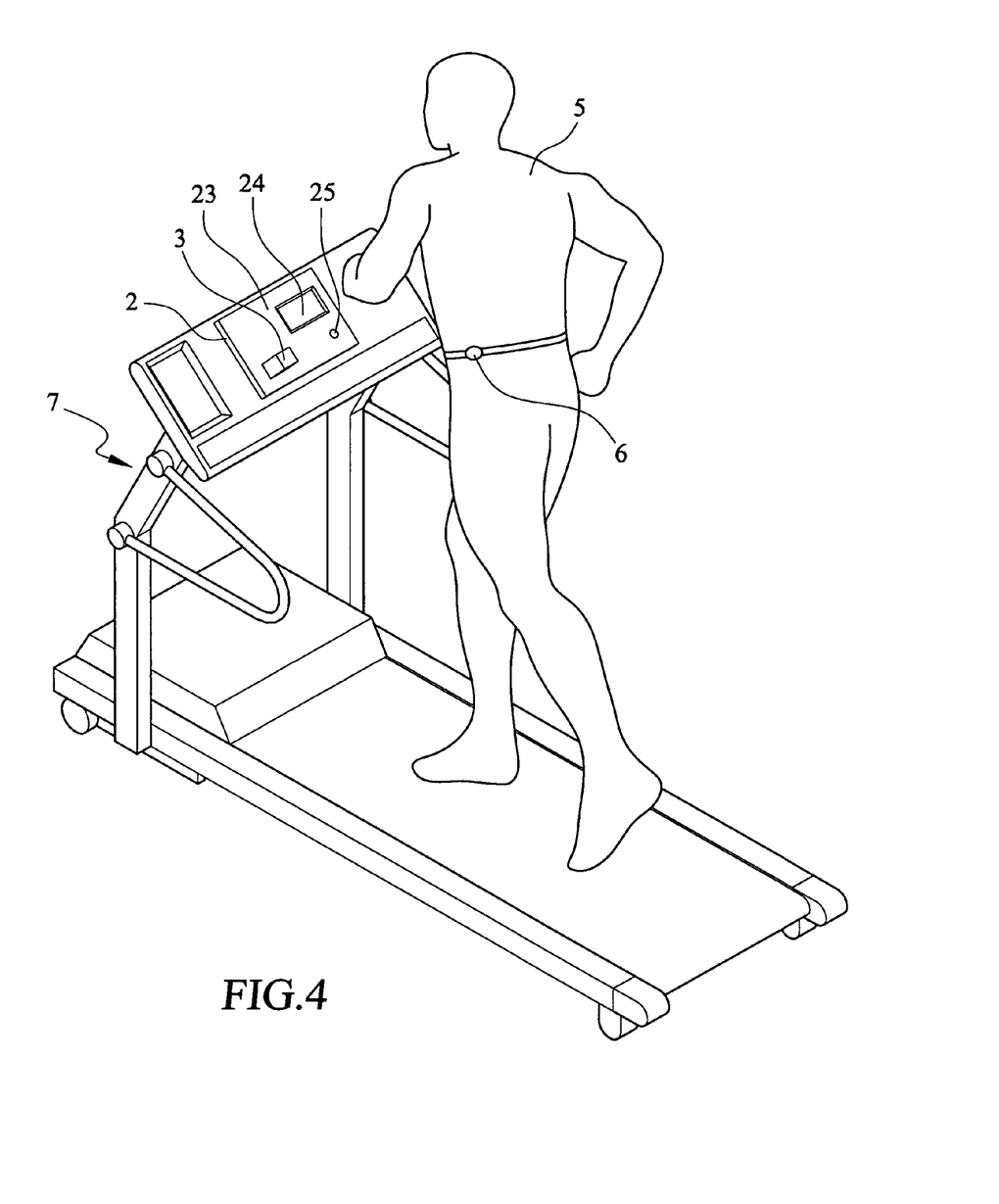
FIG. 4 is a perspective view showing that the wireless motion monitoring device of the present invention is applied to a jogging machine.

In the application shown in FIG. 3, a wireless pedometer module 6 is fitted to a foot of the user 5. The wireless pedometer module 6 may be fastened to the waist of the user 5 when he takes exercise with a jogging machine as shown in FIG. 4 or a climbing machine. In the application of FIG. 3, when the user 5 steps on the pedal of the exercise bicycle 4, the wireless pedometer module 6 measures the paces of the user 5 and generates a pace signal which is transmitted wirelessly by a wireless transmitter mounted in the wireless pedometer module 6. The pace signal is received by the motion signal receiving module 3 in the equipment control module 2 on the exercise bicycle 4 and then displayed on the display unit 24 on the panel 23 of the equipment control module 2.

The transmission activating button 25 arranged on the panel 23 of the equipment control module 2 is able to transmit an activation signal to activate the wireless pedometer module 6 to transmit the pace signal to the motion signal receiving module 3 for display, calculation, recording and analysis.

FIG. 4 is a perspective view showing that the wireless motion monitoring device of the present invention is applied to a jogging machine. As shown, the wireless pedometer module 6 is fitted to the waist of the user 5 jogging on the jogging machine 7. The equipment control module 2 of the jogging machine 7 incorporates the plug form motion signal receiving module 3 as shown in FIG. 2. Alternatively, the equipment control module 2 of the jogging machine 7 may incorporate the card form motion signal receiving module 1 as shown in FIG. 1.

In the application, the wireless pedometer module 6 counts the paces of the user 5 and sends a pace signal wirelessly by means of the wireless transmitter in the wireless pedometer module 6. The pace signal is received by the motion signal receiving module 3 in the equipment control module 2 and then displayed on the display unit 24 on the panel 23 of the equipment control module 2.

Figure 5:
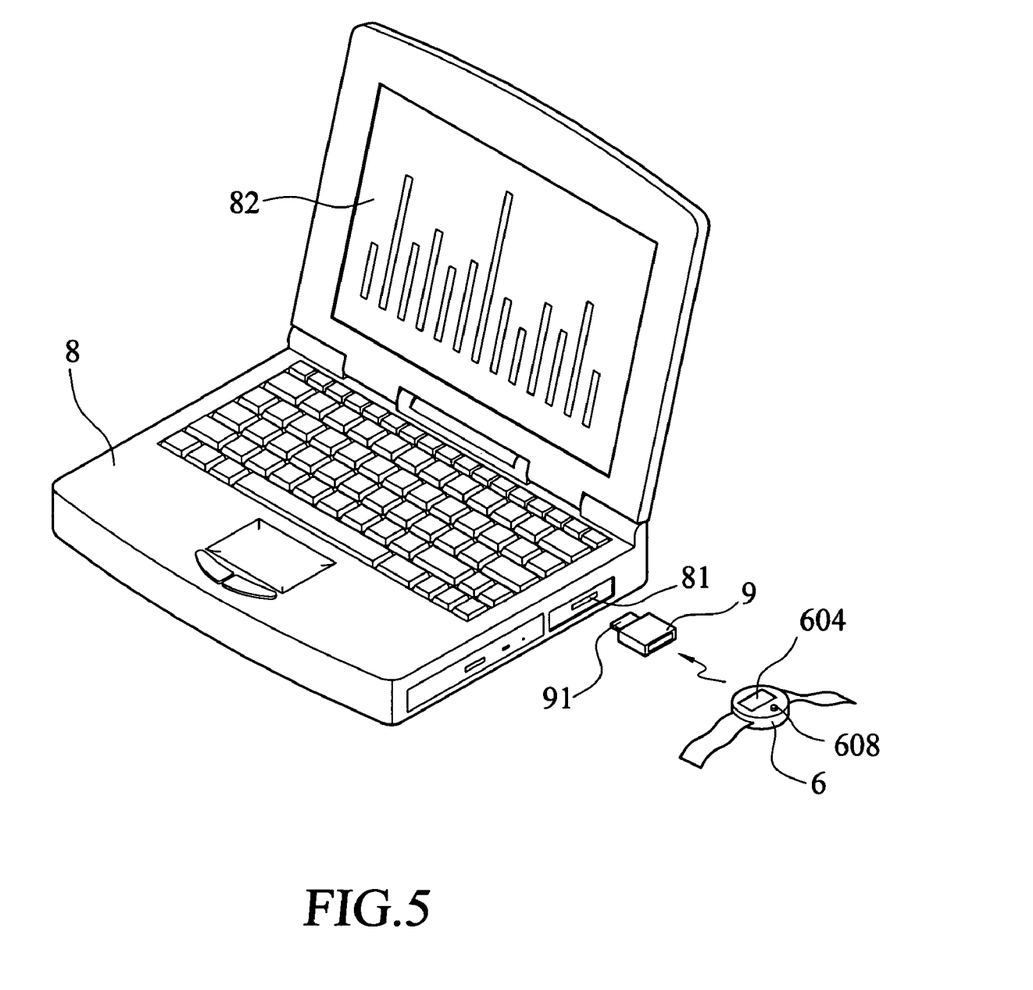
FIG. 5 is a perspective view showing that a computer device receives and processes a pace signal from the motion signal receiving module connected to the computer device.

FIG. 5 is a perspective view showing that the motion signal receiving module is coupled to a host device such as a computer device by a connection port such that the computer device receives the pace signal received by the motion signal receiving module. In the embodiment, the computer device 8 is equipped with a connection port 81 which may be a Universal Serial Bus (USB) port or an infrared communication port. By means of the connection port 81, a port adapter form motion signal receiving module 9 including a USB plug 91 can be plugged to the connection port 81 of the computer device 8. The motion signal receiving module 9 receives the pace signal transmitted wirelessly by the wireless pedometer module 6 and forwards it to the computer device 8. Moreover, the wireless pedometer module 6 is provided with a display unit 604 and a transmission activating button 608. The wireless pedometer module 6 may be provided with two straps for fastening to the user's hand, waist or feet.

After the computer device 8 receives the pace signal via the connection port 81, the computer device 8 processes the pace signal by a control program such that the pace signal is calculated, analyzed and recorded. Finally, the data or graphs representing the pace signal are displayed on the monitor 82 of the computer device 8.

Figure 6:
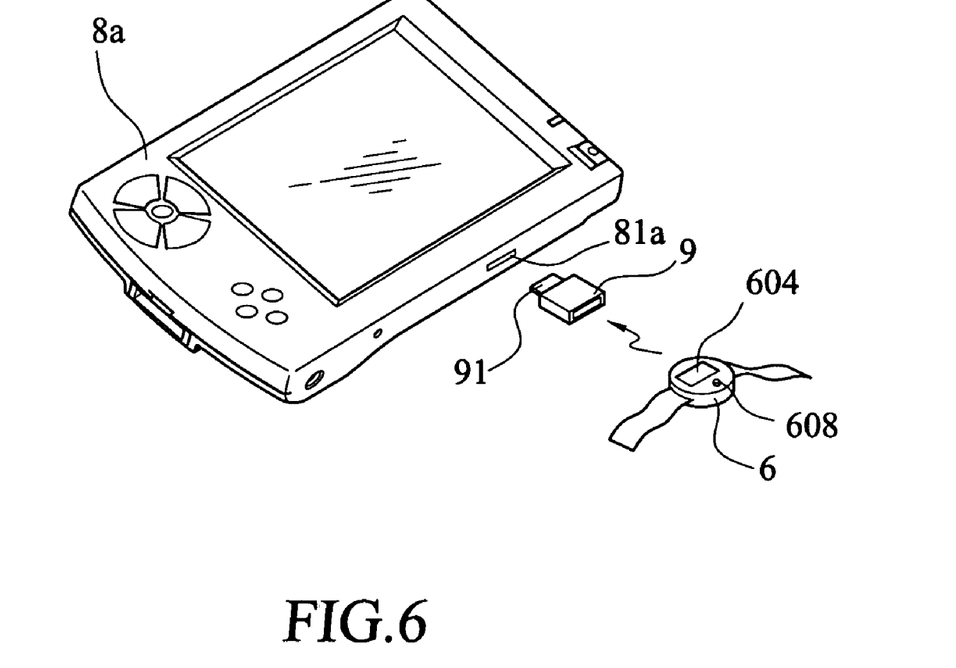
FIG. 6 is a perspective view showing that a PDA receives and processes the pace signal from the motion signal receiving module connected to the PDA.

FIG. 6 is a perspective view showing that the motion signal receiving module is coupled to a PDA by a connection port such that the PDA receives the pace signal from the motion signal receiving module. In the embodiment, the Personal Digital Assistant (PDA) 8*a* is equipped with a connection port 81*a* which may be a USB port or an infrared communication port. By means of the connection port 81*a*, a port form motion signal receiving module 9 including a USB plug 91 can be plugged to the PDA 8*a*. Similarly, the motion signal receiving module 9 receives the pace signal emitted wirelessly by the wireless pedometer module 6 and forwards it to the PDA 8*a*.

Figure 7:
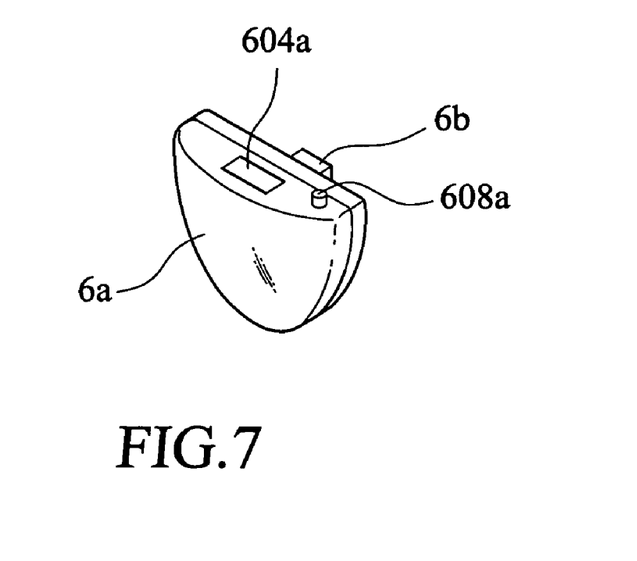
FIG. 7 is a perspective view of a wireless pedometer module of compact case form for hanging on the waist of the user.

The wireless pedometer module may be provided with a pair of straps or a flexible strap for fastening to the user. Alternatively, the wireless pedometer module 6*a* can be of compact case form as shown in FIG. 7 for securing to the user by hanging. The wireless pedometer module 6*a* is provided with a display unit 604*a*, a transmission activating button 608*a* and a hook 6*b* for hanging to the belt of the user.

Figure 8:
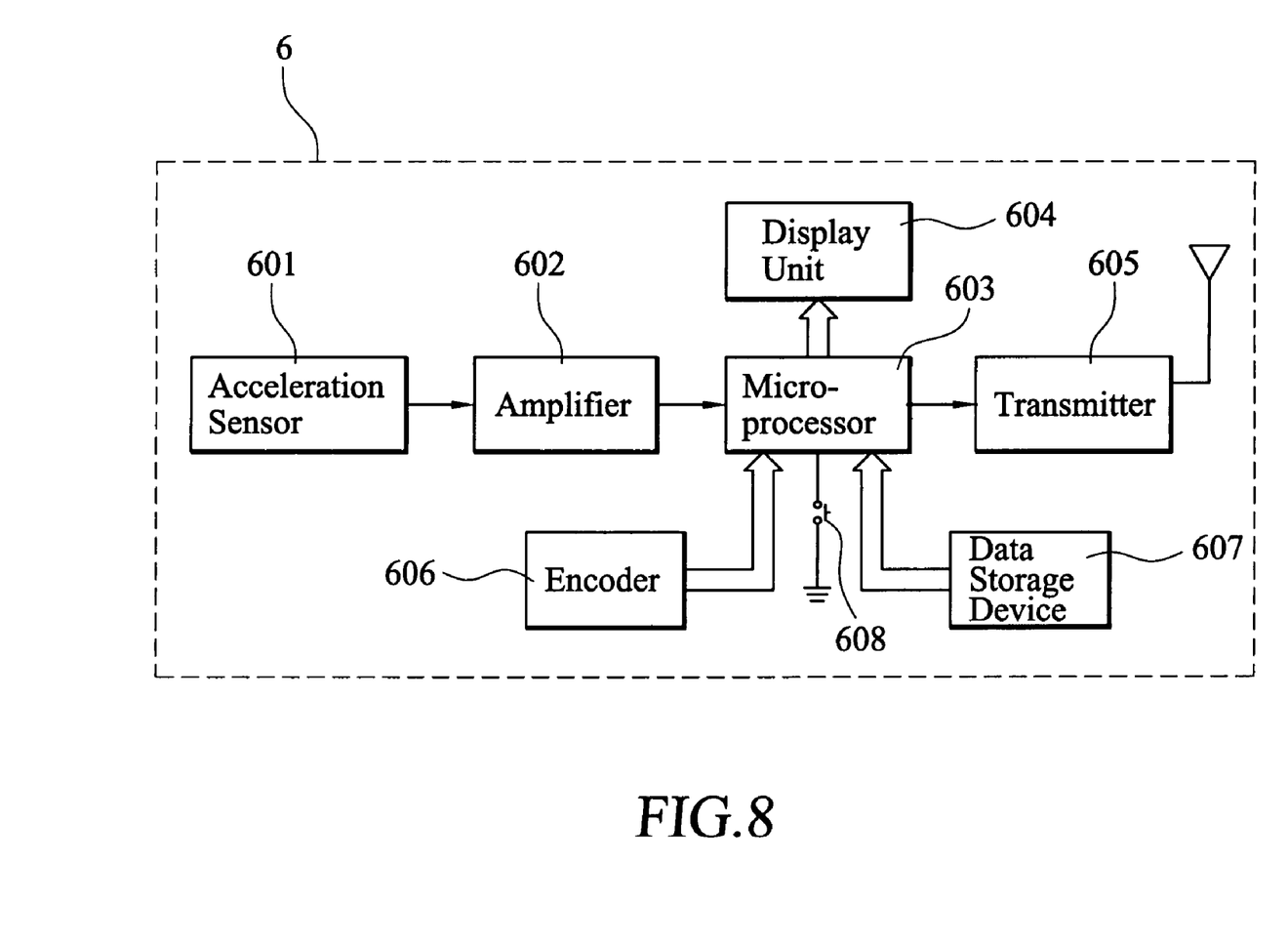
FIG. 8 is a functional block diagram of the wireless pedometer module.

FIG. 8 is a functional block diagram of the wireless pedometer module. The wireless pedometer module 6 comprises an acceleration sensor 601, an amplifier 602, a microprocessor 603, a display unit 604, a wireless transmitter 605, an encoder 606, and a data storage device 607. The acceleration sensor 601 detects the paces of the user 5 and forwards a pace signal to the amplifier 602 for amplifying.

The pace signal is then transmitted to the micro-processor 603 for processing. The processed pace signal is transmitted to the display unit 604 for displaying. The micro-processor 603 also forwards the pace signal to the wireless transmitter 605 which emits the pace signal wirelessly by radio frequency or infrared ray.

Moreover, the pace signal received by the micro-processor 603 is transmitted to the data storage device 607 for storage. Preferably, the data storage device 607 stores the user's historical records at various times or at intervals of e.g. each week, each month or each year.

The wireless pedometer module 6 also comprises a transmission activating button 608. When the user 5 presses the transmission activating button 608, the wireless pedometer module 6 emits the pace signal after detection of a predetermined number of paces e.g. 5, 10, or 15 paces to the motion signal receiving module 1 or 3.

Figure 9:
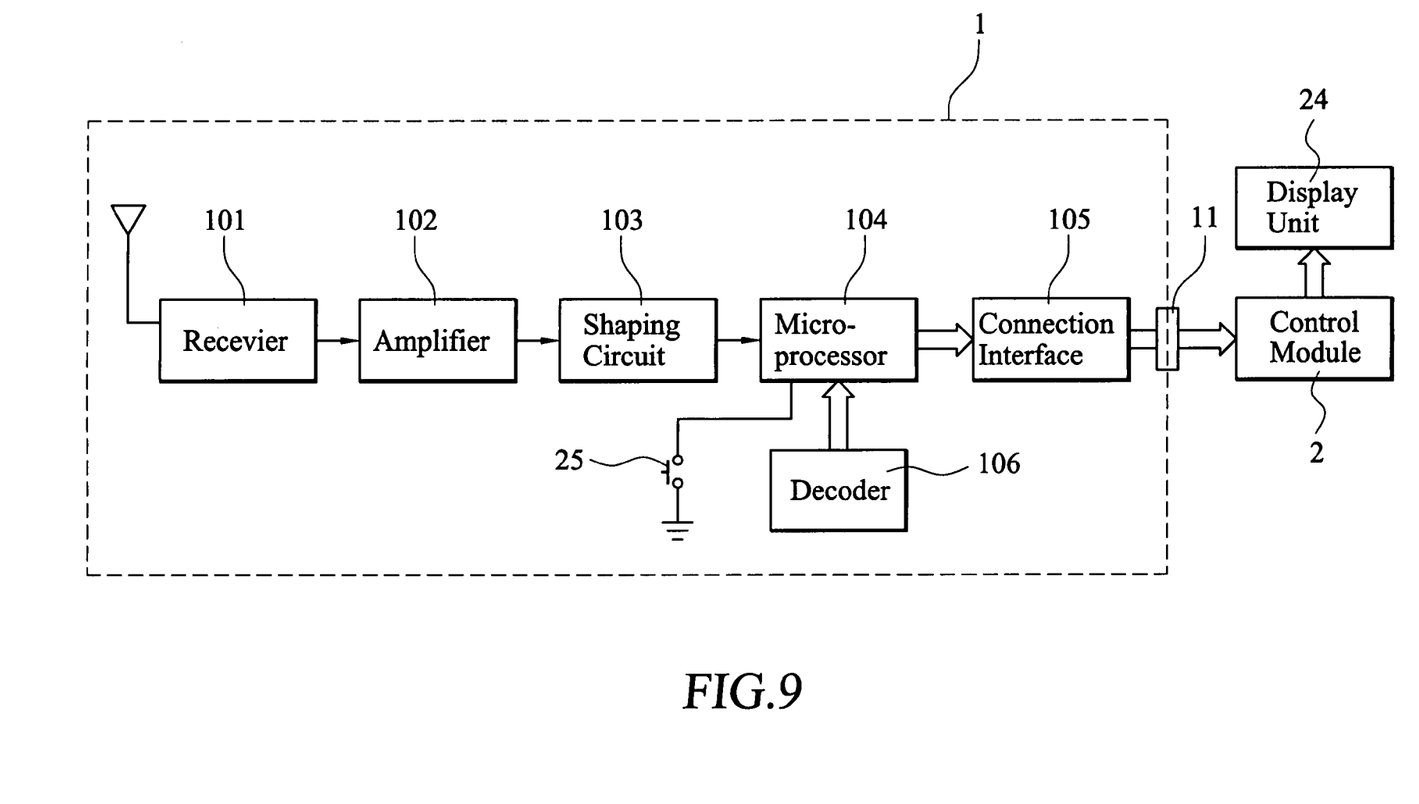
FIG. 9 is a functional block diagram of the motion signal receiving module.

Please refer to FIG. 9 which is a functional block diagram of the motion signal receiving module. The motion signal receiving module 1 comprises a receiver 101, an amplifier 102, a shaping circuit 103, a micro-processor 104, a connection interface 105, a decoder 106, and a transmission activating button 25. The motion signal receiving module 3 comprises the same components as the motion signal receiving module 1.

The receiver 101 of the motion signal receiving module 1 is able to receive the pace signal emitted wirelessly by the wireless pedometer module 6. The pace signal is then forwarded to the amplifier 102 for amplifying, and then to the shaping circuit 103 for shaping. Subsequently, the pace signal is transmitted to the micro-processor 104 for processing. The processed signal is transmitted via the connection interface 105 to the equipment control module 2 which displays the pace signal on the display unit 24.

Practically, when a plurality of motion signal receiving modules are incorporated with a plurality of exercise equipment located nearby, for example in a fitting center, mutual interference may be happened. To prevent signal interference among the exercise equipment, the wireless pedometer module 6 is provided with an encoder 606 for encoding the pace signal, while the motion signal receiving module 1 or 3 is provided with a decoder 106 for decoding the encoded pace signal, such that the motion signal receiving module 1, 3 is able to receive the pace signal only from a corresponding wireless pedometer module 6.

Figure 10:
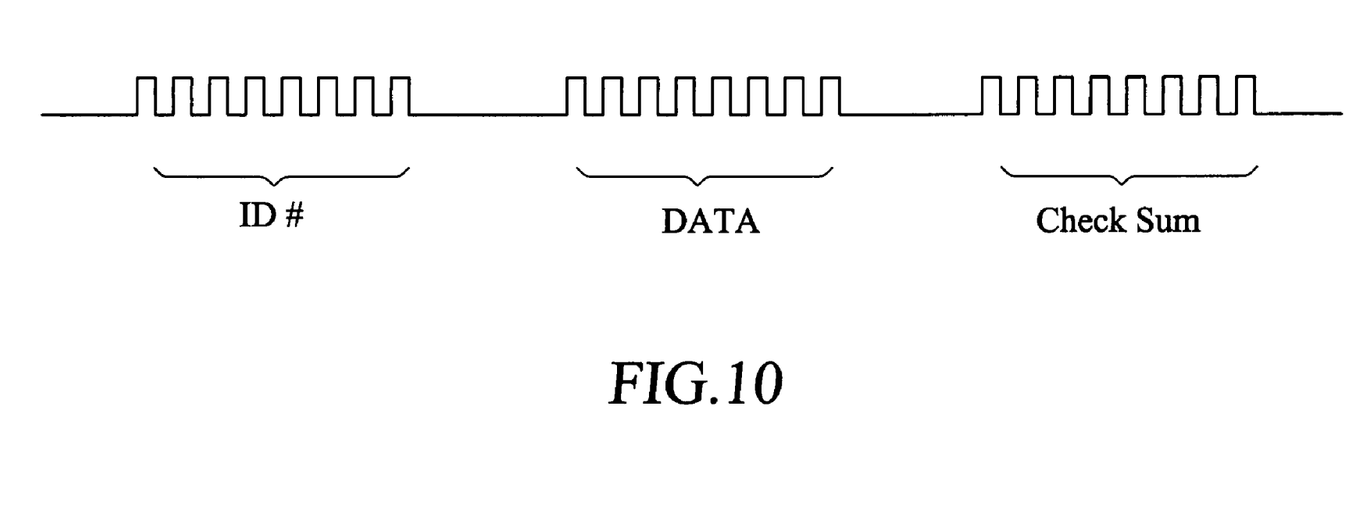
FIG. 10 is a protocol of the signal transmitted wirelessly from a transmitter of the wireless pedometer module.

With reference to FIG. 10 which shows a protocol of the signal during signal transmission. Each pace signal transmitted by the wireless pedometer module 6 includes a specific identification number ID#. When a wireless pedometer module 6 emits a pace signal wirelessly, each of the motion signal receiving modules 1, 3 located within an effective receiving distance would recognize if the pace signal comes from its corresponding wireless pedometer module 6. After the pace signal is identified by the sole corresponding motion signal receiving module 1 or 3, the motion signal receiving module 1 or 3 receives the signal DATA and checks with a check sum to eliminate error.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A wireless motion monitoring device adapted to be incorporated in an equipment control module of an exercise equipment for monitoring a motion of a user, the equipment control module being provided with a circuit board, a socket electrically connected to the circuit board, and a display unit, comprising:

a wireless motion signal detecting module having a sensor for detecting at least one motion signal of the user and transmitting the motion signal;

a data storage device disposed in the wireless motion signal detecting module for storage of the motion signal detected by the wireless motion signal detecting module for establishing historical records thereof;

a wireless transmitter arranged in the wireless motion signal detecting module for wirelessly transmitting the motion signal detected by the sensor of the wireless motion signal detecting module and the historical records;

a motion signal receiving module, in a form of a card having a connector adapted to plug into the socket of the equipment control module; and     a wireless receiver arranged in the motion signal receiving module for receiving the motion signal and historical records transmitted from the transmitter of the wireless motion signal detecting module;

wherein when the wireless receiver of the motion signal receiving module receives the motion signal transmitted from the wireless motion signal detecting module, the motion signal receiving module sends the motion signal to the equipment control module of the exercise equipment to display the motion signal on the display unit of the equipment control module.

2. The wireless motion monitoring device as claimed in claim 1, wherein the wireless motion signal detecting module further comprises a transmission activating button, and when the transmission activating button is actuated, the wireless motion signal detecting module transmits the motion signal detected to the motion signal receiving module.

3. The wireless motion monitoring device as claimed in claim 2, wherein the wireless motion signal detecting module transmits the motion signal after a predetermined plurality of motion signals are detected.

4. The wireless motion monitoring device as claimed in claim 1, wherein the historical records are stored at a predetermined interval selected from weekly, monthly or yearly.

5. The wireless motion monitoring device as claimed in claim 1, wherein the motion signal receiving module further comprises a transmission activating button, and when the transmission activating button is activated, the motion signal receiving module activates the wireless motion signal detecting module to transmit the detected motion signal to the motion signal receiving module.

6. A wireless motion monitoring device adapted to be incorporated in an equipment control module of an exercise equipment for monitoring a motion of a user, the equipment control module being provided with a circuit board, a socket electrically connected to the circuit board, and a display unit, comprising:

a motion signal receiving module having a plug adapted to plug into the socket of the equipment control module;

a wireless motion signal detecting module associated with the motion receiving module and having a sensor for detecting at least one motion signal of the user and transmitting the motion signal;

a wireless transmitter arranged in the wireless motion signal detecting module for wirelessly transmitting the motion signal detected by the sensor of the wireless motion signal detecting module with a specific identification number identifying the wireless motion signal detecting module; and a wireless receiver arranged in the motion signal receiving module for receiving a signal transmitted from the transmitter of the wireless motion signal detecting module representing the identification number and the motion signal;

wherein when the wireless receiver of the motion signal receiving module receives the signal transmitted from the wireless motion signal detecting module, responsive to the identification number identifying the received signal as corresponding to the associated wireless motion signal detecting module the motion signal receiving module sends the motion signal to the equipment control module of the exercise equipment to display the motion signal on the display unit of the equipment control module.

7. The wireless motion monitoring device as claimed in claim 6, wherein the wireless motion signal detecting module further comprises a transmission activating button, and when the transmission activating button is actuated, the wireless motion signal detecting module transmits the motion signal detected to the motion signal receiving module.

8. The wireless motion monitoring device as claimed in claim 7, wherein the wireless motion signal detecting module transmits the motion signal after a predetermined plurality of motion signals are detected.

9. The wireless motion monitoring device as claimed in claim 6, wherein the wireless motion signal detecting module comprises a data storage device for storage of the motion signal detected by the wireless motion signal detecting module for establishing historical records thereof.

10. The wireless motion monitoring device as claimed in claim 9, wherein the historical records are stored at a predetermined interval selected from weekly, monthly or yearly.

11. The wireless motion monitoring device as claimed in claim 6, wherein the motion signal receiving module further comprises a transmission activating button, and when the transmission activating button is activated, the motion signal receiving module activates the wireless motion signal detecting module to transmit the detected motion signal to the motion signal receiving module.

12. A wireless motion monitoring device adapted to be incorporated in a host device for monitoring a motion of a user, the host device being provided with a connection port, comprising:

a motion signal receiving module in a form of a port adapter adapted to plug into the connection port of the host device;

a wireless motion signal detecting module associated with the motion receiving module and having a sensor for detecting at least one motion signal of the user and transmitting the motion signal;

a data storage device disposed in the wireless motion signal detecting module for storage of the motion signal detected by the wireless motion signal detecting module for establishing historical records thereof;

a wireless transmitter arranged in the wireless motion signal detecting module for wirelessly transmitting the motion signal detected by the sensor of the wireless motion signal detecting module and the historical records with a specific identification number identifying the wireless motion signal detecting module; and a wireless receiver arranged in the motion signal receiving module for receiving a signal transmitted from the transmitter of the wireless motion signal detecting module representing the identification number and one of the motion signal or the historical records;

wherein when the wireless receiver of the motion signal receiving module receives the signal transmitted from the wireless motion signal detecting module, responsive to the identification number identifying the received signal as corresponding to the associated wireless motion signal detecting module the motion signal receiving module sends the motion signal to the host device to display the motion signal on the host device.

13. The wireless motion monitoring device as claimed in claim 12, wherein the wireless motion signal detecting module further comprises a transmission activating button, and when the transmission activating button is actuated, the wireless motion signal detecting module transmits the motion signal detected to the motion signal receiving module.

14. The wireless motion monitoring device as claimed in claim 12, wherein the host device is a computer device for receiving the motion signal from the motion signal receiving module.

15. The wireless motion monitoring device as claimed in claim 12, wherein the host device is a Personal Digital Assistant (PDA) for receiving the motion signal from the motion signal receiving module.

16. The wireless motion monitoring device as claimed in claim 12, wherein the wireless motion signal receiving module further comprises a transmission activating button, and when the transmission activating button is activated, the motion signal receiving module activates the wireless motion signal detecting module to transmit the detected motion signal to the motion signal receiving module.

17. The wireless motion monitoring device as claimed in claim 12, wherein the wireless motion signal receiving module further comprises a display for displaying the motion signal.

* * * * *